Figure 1:
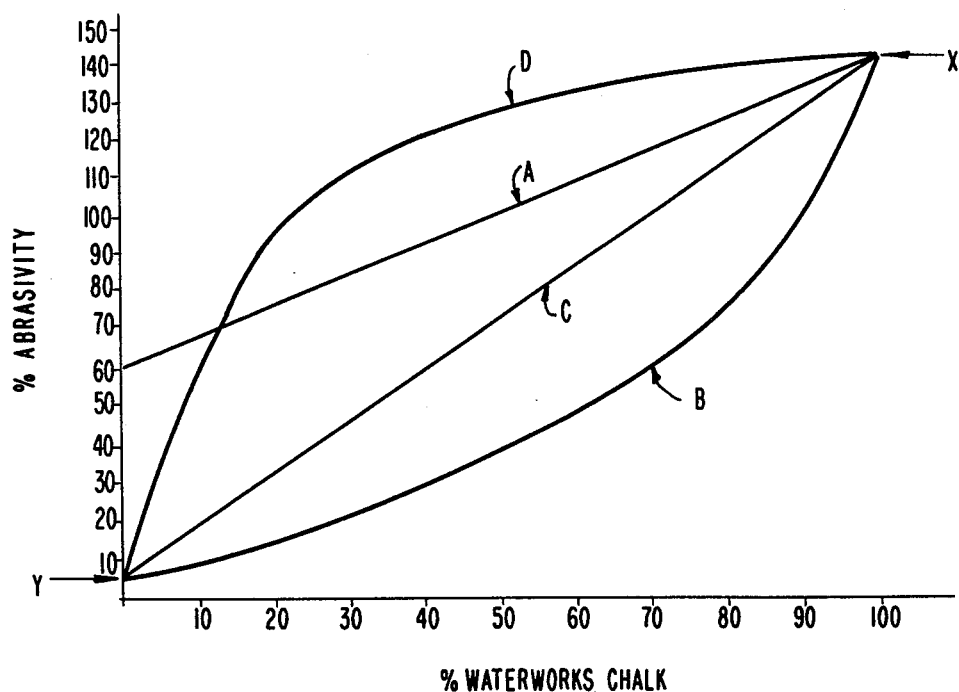
Figure 2:
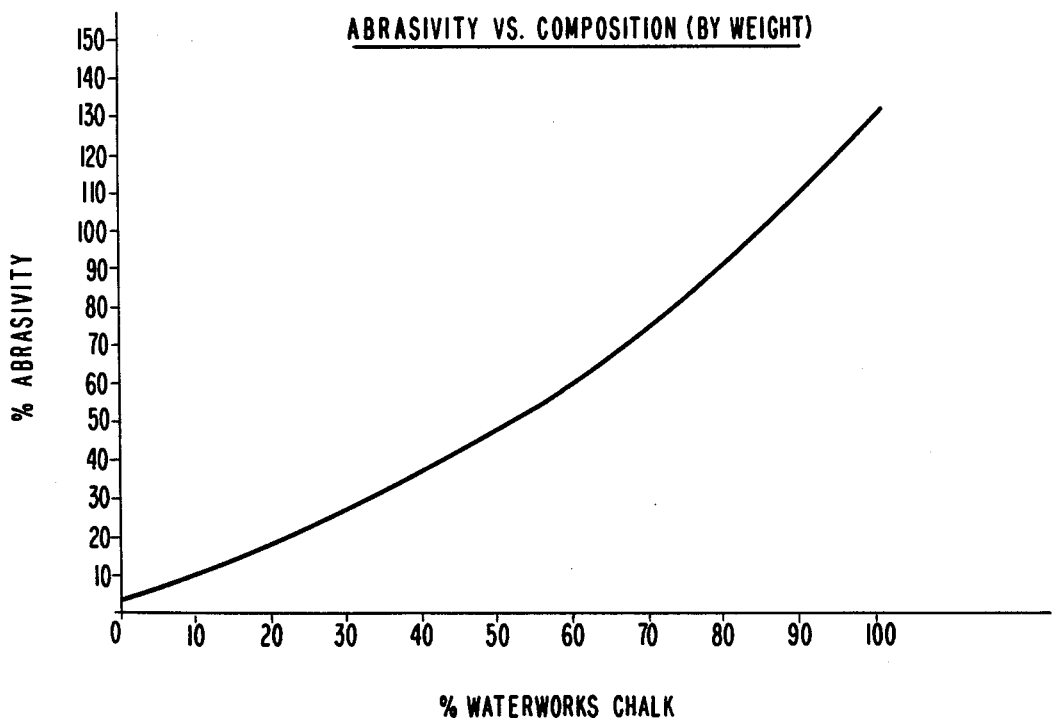

878,79.
United States Patent [19]
Davis

[11] 4,102,992
[45] Jul. 25, 1978

[54] DENTIFRICE

[75] Inventor: Walter Bryan Davis, Newdigate, England

[73] Assignee: Beecham Group Limited, Great Britain

[21] Appl. No.: 742,595

[22] Filed: Nov. 17, 1976

Related U.S. Application Data

[63] Continuation-in-part of Ser. No. 541,423, Jan. 16, 1975, abandoned.

[30] Foreign Application Priority Data

Feb. 8, 1974 [GB] United Kingdom ............... 5983/74

[51] Int. Cl.² ............................................. A61K 7/16
[52] U.S. Cl. ...................................................... 424/49
[58] Field of Search .................... 51/296, 298; 424/49–58

[56] References Cited

U.S. PATENT DOCUMENTS

| | | | |
|---|---|---|---|
| 2,196,154 | 4/1940 | Schulerud | 424/49 X |
| 3,151,027 | 9/1964 | Cooley et al. | 424/52 X |
| 3,226,297 | 12/1965 | Thuresson et al. | 424/49 |
| 3,325,368 | 6/1967 | Wood | 424/52 X |
| 3,574,823 | 4/1971 | Roberts et al. | 424/49 |
| 3,711,604 | 1/1973 | Colodney et al. | 424/52 |
| 3,803,301 | 4/1974 | Cordon et al. | 424/49 |
| 3,929,987 | 12/1975 | Colodney et al. | 424/52 |
| 3,935,306 | 1/1976 | Roberts et al. | 424/49 |

*Primary Examiner*—Shep K. Rose
*Attorney, Agent, or Firm*—Jacobs & Jacobs

[57] ABSTRACT

Dentifrice compositions containing a cleaning agent in particulate form whose abrasivitiy is reduced by incorporating a water-insoluble particulate polymeric material less abrasive than and of lower average density than the cleaning agent which is calcium carbonate. The polymeric material is typically polymethylmethacrylate or polystyrene. The respective proportions are preferably 75-99.9% to 0.1-25%, by weight. The polymeric material is in the form of particles which are not substantially agglomerated and which may be of a variety of geometrical shapes including solid and hollow spheres, cavitied or uncavitied, or composed of a lattice of material.

11 Claims, 2 Drawing Figures

DENTIFRICE

This application is a continuation-in-part of application Ser. No. 541,423, filed Jan. 16, 1975 and now abandoned.

This invention relates to a dentifrice and in particular to a dentifrice containing an abrasive having its abrasivity reduced by the addition of certain particulate materials.

A basic requirement of an effective dentifrice is that it should clean the teeth by reducing the amount of, or removing, deposits of food debris, acquired pellicle, plaque and calculus. Accordingly, a satisfactory dentifrice always includes an abrasive agent. The abrasive agent must remove these dental deposits without excessively abrading the underlying tooth material, namely the tooth enamel and dentine. The abrasivity of a particular cleaning agent is governed by physical properties such as size, shape, strength and brittleness, in addition to hardness. Dentifrice abrasives are chosen with combinations of these properties which result in the abrasion necessary for the cleaning process, with the minimum abrasion of the tooth surface.

Price is second important factor in the choice of a dentifrice abrasive. Thus, fine modifications of the physical properties of abrasive agents are unacceptable as they produce of dentifrice compositions which are too expensive to be practical. For example calcium carbonate, a commonly used abrasive is readily available, is inexpensive and a suitable basic abrasive to be widely used in toothpastes. It is obtainable in different grades varying in crystalline form, particle size, surface area, and density. Its abrasive and cleaning properties can be modified by blending different grades or mixing with other abrasive materials such as phosphates, but in general such methods of modifying cheap materials like calcium carbonate, however, lead to a very much more expensive product.

This invention is based on the discovery that the abrasivity of a coarse grade of calcium carbonate drops dramatically when a surprisingly small quantity of water-insoluble particulate organic polymer which is less abrasive and of lower average density than the calcium carbonate is added. The addition of such small quantities of polymer has the added benefit of reducing the scratch depth on dental enamel and hence improving the polishing effect of the calcium carbonate on teeth.

The present invention therefore provides a dentifrice composition comprising a cleaning agent which consists of from 75–99.9% by weight of calcium carbonate and from 0.1–25% by weight of a water-insoluble particulate polymeric material which is (a) less abrasive and (b) of lower average density than said calcium carbonate.

The polymeric materials suitable for this invention are of relatively lower abrasivity than the calcium carbonate, as measured by the Talysurf method (see British Dental Journal, Vol. 133, No. 2, pp 60–66, July 1972). In addition, it is preferred that the polymeric material has a Moh's hardness of 3 or less.

Preferred polymeric materials are thermoplastic resins, that is those which can be melted and resolidified without losing their original properties. The properties of such resins, being of relatively low hardness and rigidity, make them ineffective alone as cleaning agents in dentifrices, but ideal for the purposes of the present invention. Examples of suitable thermoplastic resins include acrylics such as polymethyl methacrylate and polyisobutyl methacrylate, cellulosics such as cellulose acetates and butyrate, polyamides, polyethylene, polypropylene, polystyrene, vinyls such as polyvinyl chloride and co-polymers of polyvinylchloride and polyvinyl alcohol.

Preferred materials are polymethyl methacrylate and polystyrene.

Such polymeric materials are present in the dentifrice in particulate form, i.e. the polymer is present as discrete particles not dissolved in the body of the toothpaste and not substantially agglomerated. The particles may be solid or composed of a lattice of material, or may be hollow. Hollow particles or particles having cavities are particularly preferred as such structures provide a less dense material. Preferred materials are based on polystyrene or polymethylmethacrylate.

The particles of polymeric material should preferably have a weight median diameter of not greater than 100 microns. The weight median diameter (W.M.D.) is that particle diameter above which 50% by weight occur. The limit of 100 $\mu$ for the WMD ensures that the particles do not impart a noticeably gritty taste to the dentifrices. A preferred W.M.D. for the particles is in the range of 0.01–50 $\mu$.

The shape of the polymer particles is not critical for the reduction of abrasivity of the calcium carbonate. Thus, spherical polymer particles or irregular granules are equally effective in this respect.

This invention is particularly useful for coarser, cheap forms of calcium carbonate which have exceptionally good cleaning power, and low abrasivity with respect to tooth enamel.

A further benefit is derived from the incorporation of polymer in calcium carbonate dentifrices which contain fluoride, either as fluorophosphate or a fluoride ion. It is well-known that fluorophosphate or fluoride complexes with calcium carbonate, thereby reducing the available fluoride activity. Our own data indicate that when calcium carbonate plus 25% or less of polymer particles is used as the abrasive agent in a fluoride dentifrice, the fluoride activity is enhanced relative to the same dentifrice containing calcium carbonate alone as the abrasive.

The curve B shows the abrasivity variation for mixtures of waterworks chalk and "Amberlite XE - 223A" obtained from Rohm and Haas and described as a co-polymer of 95% styrene, 2% ethyl vinyl benzene and 3% divinyl benzene. The polymer was supplied as spherical particles, particle size between 2 and 70 microns with a macroporous structure, pore size 100–600 Å.

The waterworks chalk/polymer particle slurries were tested on three dentine blocks by the Talysurf technique, using a total of 4g of particulate material in 11g of carrier fluid.

Table I shows the abrasivity data generated and concentration of waterworks chalk used in Gravimetric terms. The results have been expressed as a percentage of Freshmint. Curve B of FIG. 1 presents the findings graphically.

TABLE 1

| % Chalk in Chalk polymer blends | Abrasivity as % Freshmint | | Abrasivity anticipated for the chalk content |
|---|---|---|---|
| | Mean | Median | |
| 50 | 39.0 | 30.5 | 120 |
| 70 | 86.1 | 90.1 | 132 |
| 90 | 137.2 | 125.1 | 139 |

It will be seen from FIG. 1 that the substitution of small proportions by weight of cavitied polystyrene particles for waterworks chalk produces large reductions in abrasivity. Thus an abrasivity of 100 is achieved with a mixture only 20% of polymer to 80% of waterworks chalk.

The reason for this dramatic effect is illustrated by the line C which represents mixture of waterworks chalk and polystyrene measured in terms of their proportions by volume. This shows a linear decrease in abrasivity as a given volume of chalk is replaced by that volume of polymer.

The method of reducing the abrasivity of a dentifrice cleaning agent by the means described in this specification appears to be due to the fact that the polymeric material, occupies a large proportion (compared to its weight) of the active volume of the dentifrice from which the abrasive chalk particles can be used. The action of the highly abrasive particles is thereby hindered. It is, however, not merely a dilution effect, caused by there being proportionally less abrasive per unit volume when abrasive is replaced by polymer. This is proved by the curve D on FIG. 1 which represents the variation of abrasivity of the dentifrice caused by the mere removal of the waterworks chalk from the dentifrice, so that the weight of abrasive per unit volume is gradually decreased. No other abrasive or polymer is added to replace it. It can be seen that there is a very slow reduction in abrasivity until most of the chalk has been removed. A similar effect is observed if the chalk is replaced by a corresponding weight of water.

The dentifrices of this invention may be in any desired form, for example, pastes, liquids, gels, ointments, emulsions, powders, tablets, dragees or chewing gum, and comprise the additional ingredients conventionally incorporated in such preparations. Thus a toothpaste; for instance, will usually comprise, in addition to the abrasive material as cleaning agent, a detergent, humectant, binding agent, flavouring agent, preservatives and colour, and sometimes a fluoride material such as stannous fluoride, ammonium fluoride or sodium monofluorophosphate.

Commonly used dental detergents include sodium lauryl sulphate, sodium N-lauroyl sarcosinate and ricinoleate and sulphoricinoleate derivatives.

Suitable humectants include glycerol and sorbitol and also other polyalcohols such as propanediol and/or butanediol.

Binding agents are also required in toothpastes to prevent separation of ingredients on storage. Such materials are, for example, gum tragacanth, sodium carragheenate, cellulose derivatives such as carboxymethyl cellulose and cellulose ethers, polyacrylic acid and polyvinylpyrrolidone.

The dentifrice may also contain the conventional flavouring and sweetening, substances such as peppermint or spearmint oil, menthol or oils of clove, wintergreen, eucalyptus, aniseed, rose, lavender, saccharin and sodum cyclamate.

Examples of preservatives which may be incorporated into the dentifrice include p-hydroxybenzoic acid esters; hexachlorophene; and known surfactants.

If desired, colour may be imparted to the dentifrice by means of dyestuffs; or bleaches or optical brighteners may be incorporated such as sodium perborate, magnesium peroxide, hydrogen peroxide - urea compounds.

The invention is illustrated by the following Examples of toothpaste formulations containing abrasive materials according to the invention:

EXAMPLE 1

|  | % w/w |
|---|---|
| Glycerin | 30.00 |
| Sodium Carboxy Methyl Cellulose | 1.1 |
| Sodium Saccharin | 0.4 |
| Calcium Carbonate (WMD 10–15 microns) | 45.0 |
| Polymethyl methacylate Granules DV400 (WMD 40 microns) | 5.0 |
| Sodium Lauryl Sulphate | 1.5 |
| Flavour | q.s. |
| Water | to 100.00 |

EXAMPLE 2

|  | % w/w |
|---|---|
| Glycerin | 30.00 |
| Sodium Carboxy Methyl Cellulose | 0.95 |
| Calcium Carbonate (WMD 10–15 microns) | 35.00 |
| Polymethyl methacylate Granules DV400 (WMD 40 microns) | 15.00 |
| Sodium Lauryl Sulphate | 1.5 |
| Flavour | q.s. |
| Sodium Saccharin | q.s. |
| Water | to 100.00 |

What is claimed is:

1. A dentifrice toothpaste composition with minimum abrasion of tooth surface which contains as the cleaning agent 35–45% w/w of particulate coarse grade calcium carbonate weight median diameter 10–15 microns, which concentration otherwise adversely scratches dental enamel, and from 5–25% w/w of 40–100 micron organic thermoplastic water-insoluble particulate polymeric material having a Moh hardness of 3 or less in the form of particles which are not substantially agglomerated, which material is (a) less abrasive than and (b) of lower average density than the calcium carbonate and which reduces the scratch depth of the calcium carbonate on dental enamel.

2. A dentifrice toothpaste composition according to claim 1 in which the polymeric material is in the form of spherical particles.

3. A dentifrice toothpaste composition according to claim 1 in which the polymeric material is in the form of spherical particles having a particle size between 2 and 70 microns and a macroporous structure of pore size 100–600 Å.

4. A dentifrice toothpaste composition according to claim 1 in which the polymeric material is in the form of irregularly shaped spheres.

5. A dentifrice composition according to claim 1 wherein the polymeric material is polymethylmethacrylate.

6. A dentifrice composition according to claim 1 wherein the polymeric material is polystyrene.

7. A dentifrice composition according to claim 1 wherein the cleaning agent consists of 75–99.9% by weight of particulate calcium carbonate and from 0.1–25% by weight of water-insoluble particulate polymeric material.

8. A dentifrice composition according to claim 1 wherein the cleaning agent consists of from 75–99.9% by weight of particulate calcium carbonate and from 0.1–25% by weight of a water-insoluble particulate polymeric material in the form of particles which are (a)

less abrasive than and (b) of lower average density than, the calcium carbonate.

9. A dentifrice composition according to claim 8 wherein the particulate polymeric material is polymethylmethacrylate or polystyrene.

10. A dentifrice composition according to claim 8 wherein the polymeric material has a weight median diameter of from 0.01 to 50 microns and a Moh's hardness of 3 or less.

11. A dentifrice composition according to claim 8 wherein the polymeric material is present in an amount of from 0.1 to 15% by weight.

* * * * *